(12) United States Patent
Bueno Ramirez et al.

(10) Patent No.: US 11,873,331 B2
(45) Date of Patent: Jan. 16, 2024

(54) MONOCLONAL ANTIBODIES SPECIFICALLY FOR THE ANTIGEN P OF THE HUMAN RESPIRATORY SYNCYTIAL VIRUS, PRODUCED AND SECRETED BY THE CELLS HYBRIDOMAS, USEFUL FOR DETECTION AND DIAGNOSTIC OF THE INFECTION CAUSED BY RSV

(71) Applicant: PONTIFICIA UNIVERSIDAD CATOLICA DE CHILE, Santiago (CL)

(72) Inventors: Susan Marcela Bueno Ramirez, Santiago (CL); Alexis Mikes Kalergis Parra, Santiago (CL); Jorge Eugenio Mora Alarcon, Santiago (CL)

(73) Assignee: PONTIFICIA UNIVERSIDAD CATOLICA DE CHILE, Santiago (CL)

( * ) Notice: Subject to any disclaimer, the term of this patent is extended or adjusted under 35 U.S.C. 154(b) by 699 days.

(21) Appl. No.: 17/087,103

(22) Filed: Nov. 2, 2020

(65) Prior Publication Data
US 2021/0070844 A1  Mar. 11, 2021

Related U.S. Application Data

(62) Division of application No. 15/748,979, filed as application No. PCT/IB2016/054424 on Jul. 25, 2016, now Pat. No. 10,858,419.

(30) Foreign Application Priority Data

Jul. 31, 2015 (CL) .................................... 2152-2015

(51) Int. Cl.
| G01N 33/53 | (2006.01) |
| C07K 16/10 | (2006.01) |
| G01N 33/569 | (2006.01) |
| A61K 39/12 | (2006.01) |
| A61K 39/00 | (2006.01) |

(52) U.S. Cl.
CPC .......... *C07K 16/1027* (2013.01); *A61K 39/12* (2013.01); *G01N 33/56983* (2013.01); *A61K 2039/55566* (2013.01); *C07K 2317/56* (2013.01); *C12N 2760/18534* (2013.01); *G01N 2800/12* (2013.01)

(58) Field of Classification Search
None
See application file for complete search history.

(56) References Cited

U.S. PATENT DOCUMENTS

| 6,395,469 B1 * | 5/2002 | Sanhueza | C12N 7/00 435/7.1 |
| 2007/0140966 A1 * | 6/2007 | Chang | B82Y 10/00 424/1.49 |
| 2010/0278813 A1 | 11/2010 | Young et al. | |
| 2011/0287444 A1 | 11/2011 | Kanamori et al. | |
| 2013/0266600 A1 | 10/2013 | Jin et al. | |
| 2014/0348858 A1 | 11/2014 | Kalergis Parra et al. | |

FOREIGN PATENT DOCUMENTS

WO       96/16974 A1    6/1996

OTHER PUBLICATIONS

Lu et al; The major phosphorylation sites of the respiratory syncytial virus phosphoprotein are dispensable for virus replication in vitro; J. Virol.; 2002; vol. 76; No. 21; pp. 10776-10784.
International Search Report and Written Opinion dated Apr. 4, 2017 for PCT/IB2016/054424.

* cited by examiner

*Primary Examiner* — Gary Counts
(74) *Attorney, Agent, or Firm* — LUCAS & MERCANTI, LLP

(57) ABSTRACT

Monoclonal antibodies or fragments thereof are disclosed, which are binding to the protein P of the human Respiratory Syncytial Virus (RSV) which has a variable region of the heavy chain which has a sequence with at least a 90%, 95% or 99% of identity with the SEQ ID No: 1 or SEQ ID 5 or a variable region of the light chain which has a sequence with at least a 90%, 95% or 99% of identity with the SEQ ID No:2 or SEQ ID No: 6. Also provided are diagnostic methods ex vivo or in vitro for detection of the viral antigen P of RSV, in which are used the monoclonal antibodies produced and secreted by the hybridomas 2E6/D2 and 6H5/H1. The invention can be used in detection for RSV kits, having the antibodies produced by the mentioned hybridomas.

14 Claims, 5 Drawing Sheets
Specification includes a Sequence Listing.

A

B

MONOCLONAL ANTIBODIES SPECIFICALLY FOR THE ANTIGEN P OF THE HUMAN RESPIRATORY SYNCYTIAL VIRUS, PRODUCED AND SECRETED BY THE CELLS HYBRIDOMAS, USEFUL FOR DETECTION AND DIAGNOSTIC OF THE INFECTION CAUSED BY RSV

CROSS REFERENCE TO RELATED APPLICATION

This Application is a divisional of U.S. application Ser. No. 15/748,979, filed on Jan. 30, 2018, now U.S. Pat, No. 10,858,419 which in turn is a 371 of PCT/IB2016/054424 filed on Jul. 25, 2016, which claims priority of Chilean Application No. 2152-2015 filed Jul. 31, 2015, each of which are incorporated herein by reference.

FIELD OF THE INVENTION

The present invention refers to monoclonal antibodies, or fragments thereof, which recognize the protein P of the Human Respiratory Syncytial Virus (RSV), useful for developing diagnostic methods of RSV infection in humans.

STATE OF THE ART

Respiratory diseases caused by virus are a public health problem around the world. The main responsible of these infections in the pediatric population are: the Human Respiratory Syncytial Virus (RSV), Adenovirus (ADV), Influenza Virus A and B (INF A and B), Parainfluenza Virus (PIV) and the Human Metapneumovirus (MPV). Currently, there is not effective mechanisms of prevention against these viruses and it is daily generated an estimated of 94,000,000 of new cases (World Health Organization). The supersaturation of the health systems associated to the outbreaks, generates also substantial economic lost.

The RSV is a virus, which affects the respiratory system and currently represents a problem of great economic and social relevance, affecting with high levels of morbidity and mortality to children and elderlies. In these populations, especially in infants and children under two years, RSV causes a wide variety of clinical profiles, from milder forms as rhinitis, tonsillitis and otitis, and other more severe forms as pneumonia, bronchitis, bronchiolitis and alveolitis. Serological studies estimates between 70% and 100% of the children have been exposed at least once to the virus at the age of 1 and 2 years, respectively. It has been estimated that annually RSV causes an approximate of 34 million of infections, 3.4 million of hospitalizations and about 200 thousand deaths in children under 5 years. Currently, RSV is a virus of epidemiology relevance in Chile and Latin America. Some studies have demonstrated that the percentage of cases of respiratory infections caused by RSV in neonates and infants can be higher than the 70% during the winter outbreaks. Moreover, studies in Latin America, reinforce the RSV role as infectious main agent responsible of infections of the respiratory lower tract in individuals under 2 years, with a reported incidence of more than 40%. Unfortunately, nowadays there are not approved vaccines for immunizing neonates, nor efficient treatments for controlling the infection of this population.

RSV is an RNA virus of approximately 15.3 kb, encapsulated, with single strand genetic material and negative coding polarity, belonging to the Paramyxoviridae family and to the *Pneumovirus*. The RSV genome codes 10 genes sorted in the following way 5'-NS1-NS2-N-P-M-SH-G-F-M2-L-3', which are transcribed by the RNA-dependent RNA polymerase (protein L) in 10 RNA independent messengers.

Five of these proteins are responsible of the packing of the genetic material and of defining the own structure of the viral particle, corresponding to the protein of nucleocapsid N and the protein of matrix M, along with the glycoproteins of transmembrane F, G y SH, respectively. The other four proteins, M2-1, M2-2, L and P, are involved in viral replication and transcription. Additionally, proteins NS-1 and NS-2 are non-structural which reduce the interferon expression of type I by the infected cell and, therefore, they prevent the activation of the innate immune response.

In the Public Health services the current diagnostic methods include a test based on the detection of viral antigens for direct Immunofluorescence in nasopharyngeal swab samples, using reverse transcription polymerase chain reaction (RT-PCR) and immunochromatography test (quick tests). From the mentioned products, viral panels based on immunofluorescence are the most striking, due to the fact that they allow detecting a greatest number of respiratory viruses, being 12 types in the case of Respiratory Viral Panel (RPV) PCR utilizing LUMINEX® XTAG® (multiple immunoassays) and 14 types for the eSensor Respiratory Viral Panel. Despite this wide range of detection, it is important to note the cost and response time factors used by them. In the case of the first mentioned test, the cost is approximately 70 USD with a response time of between 12 to 18 hours, meanwhile the second test cost is approximately 90 USD and a response time of 60 minutes.

Therefore, it is fundamental to count with an effective, quick and low cost diagnostic test for detecting RSV that can compete with the features of available diagnostic methods. In response to such problem, the present invention describes monoclonal antibodies, which are a needed alternative for supplying said need, since they allow the specific recognition of viral antigens in samples from patients infected with RSV. This way, the present invention comprises products such as monoclonal antibodies, and an alternative method, which uses them for detection and a quick, effective, and accurate diagnostic in patients infected with RSV with a 100% of specificity in clinical samples and is able of detecting by ELISA concentrations equivalents to 1.5 ng of the specific antigen. This will allow to clinical professionals determine an early and suitable treatment.

A monoclonal antibody is a type of homogeneous antibody that is characterized by recognizing specifically a single antigen. They are produced by a single hybrid cell (hybridoma), which is product of the fusion of a lymphocyte B clone and a tumor plasmatic cell. The property of binding specifically to and with high affinity to an antigen has driven the monoclonal antibodies development as a very useful tool for detecting molecules, which generate a great scientific, clinical and industrial use interest. Currently, monoclonal antibodies are widely used, in both basic and applied research, due to their specificity and reproducibility, allowing better support of research. However, is in the biomedicine area where the monoclonal antibodies have had huge practical applications, either for diagnostic or for treatment of multiple infectious diseases, and as therapy for other pathologies. While is true that the monoclonal antibodies are used in all kind of detection and diagnostic techniques, is in the kits design for in vitro diagnostic where the best results have been obtained. For it, currently there are diver quick detection kits, such as the pregnant test, which is based on the determination of the chorionic gonadotropin (hCG) levels in the urine using anti hCG antibody. In addition, the monoclonal antibodies for therapeutic use have gained great relevance. Currently, there are therapeutic treatments for different pathologies, using commercial monoclonal antibody as: Alemtuzumad, Gemtuzumab ozogamicina, Rituximab, Trastumab, among others.

In the previous art there is the publication WO2013076702, which describes the use of a monoclonal antibody specific for detection of the respiratory syncytial virus, it is described specifically an antibody directed against the M2-1 antigen, generated at our laboratory (Gomez et al, J Med Virol. 2014 July; 86(7):1256-66). This antibody differs from the present invention in monoclonal antibody for RSV detection has as antigen the protein P, and not M2-1 as is described in the cited document. The advantage of generating antibodies against the protein P is that these being against an antigen different can be used in an immunoassay along with the anti M2-1 antibodies (previously published), increasing the sensitivity in detection of the antigen which is in small amounts in the nasopharyngeal samples.

Document US2014093501 describes an antibody composed by heavy and light variable chains of at least one murine monoclonal antibody, against the RSV. Specifically, the antibody is addressed to the protein F. Unlike the present invention, the monoclonal antibodies for RSV detection have the protein P as antigen, and not against F as described in the cited document. Notably, antigen P is more conserved than the antigen F, which allows detecting RSV strains that present different serotypes.

SUMMARY OF THE INVENTION

The present invention refers to a two monoclonal antibodies against the human Respiratory Syncytial Virus (RSV). Specifically, the present invention involves two murine monoclonal antibodies, corresponding to monoclonal antibodies secreted by hybridomas cell lines called 2E6/D2 and 6H5/H1, and which react against the antigen P of RSV. These antibodies do not compete with each other for the antigen binding site, nor exert an impediment for binding simultaneously to it. Said monoclonal antibodies can be used for detection assays, diagnostic and/or determination of infection by RSV. These antibodies can be used simultaneously for increasing the sensitivity of detection in clinical samples, where there is low availability of the antigen. Particularly, the antibodies from the hybridoma 2E6/D2 are able of capture efficiently the protein P of RSV in clinical samples. These proteins captured and immobilized are detected later by the antibodies generated by the hybridoma 6H5/H1, which are conjugated to an enzyme, which acts over a chromogen substrate. This quality allows the combination of both antibodies with different label for detecting the same antigen in samples where it is finding in small quantity.

The invention provides diagnostic methods ex vivo or in vitro for detection of the viral antigen P of RSV, in which are used the monoclonal antibodies produced and secreted by the hybridomas 2E6/D2 and 6H5/H1 in assays as ELISA, fluorescence microscopy, immunoblot, immunofluorescence, immunohistochemistry, immunochromatography, flow cytometry, cell sorter, immunoprecipitation and/or Western blot. The samples to analyze are selected from: in vitro cells infected with RSV, nasal secretions, nasal washes, pharyngeal secretions and/or bronchial washes or secretions, cerebrospinal liquid, plasma, among others. The invention provides a method for detection of RSV in biological samples and cell cultures, using the monoclonal antibodies produced and/or secreted by the cell lines of the hybridomas previously mentioned, coupled in any kind of solid support, as nitrocellulose, nylon membrane, magnetic beads, fluorescent beads or other support; or coupled to any other molecule, as enzymes, proteins, fluorophores, radioisotopes or any other chemical compound. The invent can be used in detection kits for RSV comprising the antibodies produced by the mentioned hybridomas. Also, the present invention comprises within its scope incorporating any kind of molecule or substrate bound chemically, such as labels, fluorophores, biotin, radioisotopes, metals, enzymes and/or any chemical element coupled to the monoclonal antibodies secreted by the hydridomas 2E6/D2 and 6H5/H1, where said molecule or substrate bound chemically allows visualizing or detecting to the antibody. This way, the invention also provides antibodies, which recognize specifically the protein P coupled to molecules or substrates or markers different from the antibody, as part of the method of detection, analysis and/or diagnostic in biological samples.

DETAILED DESCRIPTION OF THE INVENTION

Figure 1:
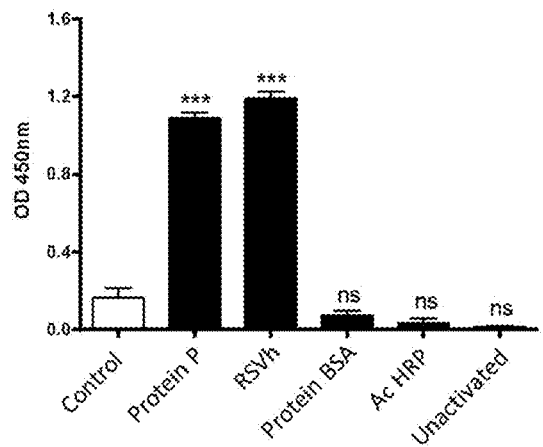
FIG. 1: Detection of protein P of RSV by the monoclonal antibodies produced by the hybridomas 2E6/D2 and 6H5/H1, using an indirect ELISA assay. The plate was activated with 50 ng of protein P of RSV purified recombinant, or with $1 \times 10^6$ pfu of RSV. As negative controls, other wells were activated with $1 \times 10^6$ pfu of Metapneumovirus (MPV) or with 50 ng of BSA protein; also wells without antigen, with primary antibody, with mouse anti-IgG conjugated with HRP (unactivated) and wells without antigen nor primary antibody, only with the mouse anti-IgG antibodies (HRP). Later, the wells were incubated with the anti-P antibody from the hybridoma 2E6/D2, in an amount of 170 ng per well (A), the hybridoma 6H5/H1 in an amount of 170 ng per well (B) and the anti-P RSVH102 Anti-Respiratory Syncytial Virus Phosphoprotein antibody, catalog number #AB94965 (Abcam) used an amount of 170 ng per well (C). The data shown in the bar chart express the detected absorbance to 450 nm, emitted by the substrate conversion tetramethylbenzidine to a colored compound, catalyzed by the Horseradish peroxidase (HRP) enzyme present in a mouse secondary antibody anti-IgG which was bound specifically to the antibodies secreted by the hybridomas 2E6/D2, 6H5/H1 and RSVH102 of Abcam. The values correspond to the average+/- the standard deviation of the emitted absorbance by each sample in at least two independent assays. *** $P<0.0001$ for the ANOVA test of one via compared to the negative control and testing using multiple comparisons pf Dunnett's, ns, there is not significate difference compared to the negative control.
Figure 1:
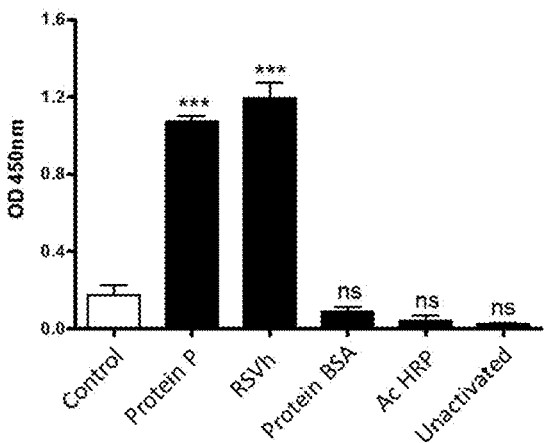
Figure 1:
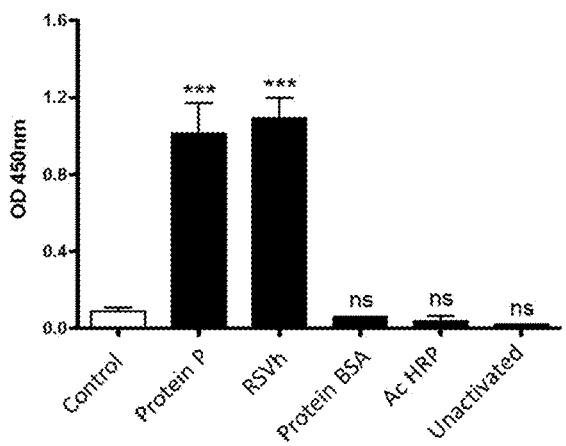

The present invention refers to a two monoclonal antibodies, or fragment thereof, the 2E6/D2 of the IgG1 isotype and 6H5/H1 of the isotype IgG2A, which recognize specifically the protein P (herein also denominated as anti-P antibodies), of the RSV.

The present invention describes two monoclonal antibodies that recognize specifically the RSV protein P. As was indicated, these antibodies are produced by the hybridomas 2E6/D2 and 6H5/H1. The aminoacids sequences of the variable regions of both antibody chains produced by the hybridoma 2E6/D2 are described in the SEQ ID No: 1 for the heavy chain and SEQ ID No: 2 for the light chain. The nucleotide sequences which encode them are described in the SEQ ID No: 3 and SEQ ID No: 4, respectively. In the same way, the aminoacids sequences of the variable regions of both antibody chains produced by the hybridoma 6H5/H1 are described in the SEQ ID No: 5 for the heavy chain and SEQ ID No: 6 for the light chain. The nucleotide sequences which encode them are described in the SEQ ID No: 7 and SEQ ID No: 8, respectively.

From these variable sequences, antibodies are constructed which comprise them, including either only one of the variable regions, or mixing them in all the possible combinations. All those embodiments are within the approach of the present invention. Namely, the present invention includes antibodies comprising at least one of the sequences SEQ ID No: 1, SEQ ID No: 2, SEQ ID No: 5 and SEQ ID No: 6 and similar sequences with up to 90%, 95% or 99% of homology or identity respecting to any of said aminoacids sequences. As well as the nucleotide sequences comprising at least one of the sequences SEQ ID No: 3, SEQ ID No: 4, SEQ ID No. 7 and SEQ ID No. 8, as well as their complementary reverses and similar sequences with up to 80%, 85%, 90%, 95% and 99% of homology or identity respecting to any of said nucleotide sequences. The greater homology degree considered in the nucleotide sequences is based on the degeneration of the genetic code. This way, the present invention includes also a set of nucleotide sequences, which encode for a monoclonal antibody, or fragment thereof, which recognizes specifically the RSV protein P.

In an specific embodiment of the invention, said antibodies or fragments thereof are conjugated with a label which allows its detection, such as, biotin, metals, enzymes, proteins, fluorophores, radioisotopes or any other chemical compound.

In another specific embodiment of the invention, said antibodies or fragments thereof are murine or humanized antibodies.

As is shown in the figures, these antibodies do not react with other proteins or molecules present in related virus or samples of patients with other virus associated to respiratory infections. This decreases notably the possibility of false negatives when are used in diagnostic methods.

The invention provides also diagnostic methods ex vivo or in vitro and detection of the RSV viral P antigen in a biological sample, in which are used the monoclonal antibodies produced and secreted by the hybridomas 2E6/D2 and 6H5/H1 in detection assays of binding of the antibody with the antigen.

The method comprises contacting a biological sample selected from: cells in vitro infected with RSV, runny nose, nasal washes, pharyngeal secretions and/or bronchial washes or secretions, among others, with the monoclonal antibody against RSV or a fragment of it secreted by the hybridomas 2E6/D2 and 6H5/H1, and then detecting the binding of the antibody with the antigen with a selected assay of: ELISA, fluorescence microscopy, immunoblot, immunofluorescence, immunohistochemistry, immunochromatography, flow cytometry, cell sorter, immunoprecipitation and/or Western blot.

Also the method of the present invention comprises antibodies or fragments thereof produced and/or secreted by the cell lines of the hybridomas mentioned above, coupled with any other kind of solid support, as nitrocellulose, nylon membrane, magnetics beads, fluorescent beads or other support. In another specific embodiment of the invention, the antibodies or fragments thereof used in the method are conjugated with a label which allows its detection, such as biotin, metals, enzymes, proteins, fluorophores, radioisotopes or any other chemical compound.

The invention also describes a kit of detention for RSV comprising at least one antibody produced by the mentioned hybridomas. In a specific embodiment of the invention, the antibodies or fragments thereof produced and/or secreted by the hybridomas cell lines previously mentioned used in said kits, are coupled with any kind of solid support, as nitrocellulose, nylon membrane, magnetics beads, fluorescent beads or another support. In addition, in a specific embodiment of the invention, the antibodies or fragments used in the kit are conjugated with a label that allows its detection, such as biotin, metals, enzymes, proteins, fluorophores, radioisotopes or any other chemical compound.

In another specific embodiment of the invention, the kit of diagnostic correspond to a immunochromatographic test, LUMINEX® (multiple immunoassays), flow cytometry, immunofluorescence, radioimmunoassay, Western blot, Dot plot, ELISA, immunodiffusion or immunoprecipitation. This way, the invention provides also antibodies that recognize specifically the protein P coupled to molecules or substrates or labels different from the antibody, as part of the detection method, analysis and/or diagnostic in biological samples.

Following are described examples that allow demonstrating the different applications of the monoclonal antibodies of the invention.

EXAMPLES

Example 1: Obtaining Purified RSV Protein P

For obtaining the purified RSV protein P, was performed an expression strategy of heterologous form (recombinant) in the bacterium *Escherichia coli* BL21. For this, the RNA was extracted of cell cultures HEp-2 infected with RSV and the gen, which encodes for the protein P was amplified by PCR and cloned in a bacterial expression vector (pET15b), which allowed controlling the gene expression cloned using the inductor molecule Isopropyl β-D-1-thiogalactopyranoside (IPTG). As purification strategy for recombinant proteins, the used expression vector possess an insert which encodes for six consecutive Histidines, so that when overexpression of the proteins was inducted, these expressed in their C-terminal end the 6 consecutives His. The advantage of using said energy is that, the protein acquires a characteristic electric charge, which allowed its purification through the affinity chromatography to a suitable pH. The purification of the recombinant proteins with histidine tales was achieved by elusion with a tampon solution, which contains imidazole, analogue to the histidine, which competes with the proteins for the binding sites in a resin column, charged with Ni+.

Finally, the purified samples were analyzed using SDS-PAGE gels.

Example 2: Production of Hybridomas, Product of the Fusion of a Clone of Lymphocyte B and a Tumor Plasmatic Cell The production of hybridomas was made using the mice immunization BALB/c with 1 mg of antigen (RSV purified recombinant protein P emulsified in adjuvant of Freund), with a purity greater than 50%. After the immunization, the mouse that presented the higher title of antibodies in the serum was selected, and it was given another booster injection. Three days after its splenic lymphocytes were isolated for making a somatic fusion with cells of the myeloid cell line NSO/2 non-secreting. The hybridomas produced were seeded in 96-wells plates in a selective medium containing Hypoxanthine, Aminopterin and Thymidine (HAT). After 10 days the supernatant of the viable hybridomas was evaluated by ELISA for detecting antibodies against the antigen used for immunization. The positive hybridomas were expanded to 24-wells plates for generating a greater volume of supernatants, which later were used for making characterization assays (specificity, sensitivity, efficiency). Finally, the hybridomas with higher specificity were cloned by limit dilution, i.e., successive dilutions of a cell suspension were made, until getting an aliquot that contained a single cell. Later, ascites fluids were prepared in mice and was determined the subclass of each monoclonal antibody. The concentration of the generated monoclonal antibodies was determined by ELISA, incubating the antibodies in different concentrations and using a mouse monoclonal antibody anti-Melan A (Santa Cruz Biotechnology, Dallas, Tex.) for preparing the standard curve.

Example 3: Determination of the nucleotide sequence that encodes the light (VL) and heavy (VH) chains of the variable region of the RSV anti-P antibody secreted by the hybridoma 2E6/D2 and of the RSV anti-p antibody secreted by the hybridoma 6H5/H1.

The following protocol was used for the hybridomas 2E6/D2 and 6H5/H1 separately. The hybridoma was grown in the middle of culture DMEM-high glucose supplemented with 3.7 g/L of Sodium Bicarbonate and 10% fetal bovine serum, to 37° C. with 10% CO2, until a cell density of 700,000 cells/ml. The total RNA of $3.5 \times 10^6$ cells was obtained, making a treatment with the Trizol (Invitrogen) compound. 0.5 μg of RNA was used for generating the cDNA using retrotranscription reaction with the Impron II (Promega) kit. Using PCR the variable region was amplified of the genes, which encode the kappa and lambda chains of the immunoglobulins. For this, the universal primers of the Ig Primer set of Novagen (catalogue number 69831-3) kit were used and the manufacturer instructions were followed.

The variable region of the light chain was amplified with the primers MuIgKVL5'-B: 5'ACTAGTCGACATG-GAGWCAGACACACTSCTGYTATGGGT3' (SEQ ID NO: 10) and the heavy chain was amplified with the primers MuIgVH5'-A: 5'GGGAATTCATGRASTTSKGGYT-MARCTKGRTTT3' (SEQ ID NO: 11) and MuIgVH5'-F:

5'ACTAGTCGACATGAACTTYGGGYTSAGMTT-GRTTT3' (SEQ ID NO: 12). The PCR products were cloned in the cloning vector pTOPO-TA (Invitrogen) according to the manufacturer instructions and sequenced by the sequencing service of the Pontificia Universidad Catáoica de Chile in a sequencer ABI prism 3130xl (Applied Biosystem). The deducted aminoacids sequences SEQ ID NO: 1 and SEQ ID NO: 2 for the hybridoma 2E6/D2 and SEQ ID NO: 5 and SEQ ID NO: 6 for the hybridoma 6H5/H1) were obtained using the bioinformatic program Vector NTI (Invitrogen).

Example 4: RSV Antigens Detection Assay, Determination of Specificity of the RSV Anti-P Monoclonal Antibodies for Purified Antigens of RSV Using Indirect ELISA Assay This assay has as objective demonstrating the specificity for the RSV protein P of the antibodies produced by the hybridomas 2E6/D2 and 6H5/H1. The detection of the antigen was carried out using the indirect ELISA technique, where the ELISA plate was activated with 50 ng of purified antigen for 1 hour to 37° C. The same way the plate was activated with $1 \times 10^6$ plates formers units (pfu) of the RSV. As negative controls Metapneumovirus (MPV) was included under the same conditions in which the RSV was incubated, and also 50 ng of protein BSA was included in an independent well. Later, the plate was washed twice with phosphate buffered saline (PBS)/Tween 0.05%. Then, the plate was blocked for 2 hours to 37° C. with PBS/FBS 10%. Later the washes were repeated and then were incubated each one of the antibodies (2E6/D2 and 6H5/H1) to a final concentration of 3.4 µg/ml, diluted in PBS/FBS 10%, for 1 hour to environment temperature (each antibody in an independent plate). Under the same conditions, in a different plate, a control assay was made using a monoclonal antibody, which recognizes the RSV protein P (Anti-Respiratory Syncytial Virus Phosphoprotein antibody RSVH102, catalogue number #AB94965, Abcam) to a concentration of 3.4 µg/ml. After the incubation time, the washes were repeated and a mouse anti-IgG secondary antibody was added to each one of the wells labeled with the enzyme horseradish peroxidase (Horseradish peroxidase, HRP) in dilution 1 in 2,000 (25 ng per well) in PBS/FBS 10%, for 1 hour to environment temperature. Finally, the washes were made and it revealed with 50 µl of citrate buffer/Tetramethylbenzidine (TMB, 3-3'-5-5'tetramethylbenzidine, 1 mg/ml, Becton Dickinson). For stopping the reaction 50 µl of $H_2SO_4$ 2N was added and the result was read in an ELISA lector, to 450 nm. For determining that the reaction of the secondary antibody was specific in recognizing to the primary antibody and also that the obtained signal don't be provoked by unspecific binding of the secondary antibody to the viral antigen, controls were made in which was used only the secondary antibody without primary antibody nor sample (unactivated well). Another control for determining that the reaction of the primary antibody is specified for the antigen, it consisted in the use of the antibodies over an ELISA plate which has not been activated with the antigen (without antigen) or using the antibodies over an ELISA plate which had 50 ng of the protein BSA or a different virus (MPV). The results show that the monoclonal antibodies of the invention are able of recognizing 50 ng of purified antigen, specifically, since they do not recognize the protein BSA, nor proteins of another related virus (FIGS. 1A and 1B). On the other hand it was observed that the commercial antibody RSVH102 (FIG. 1C) used in the assay as control, was specific for the detection of both the virus and the protein P of the recombinant RSV.

Figure 2:
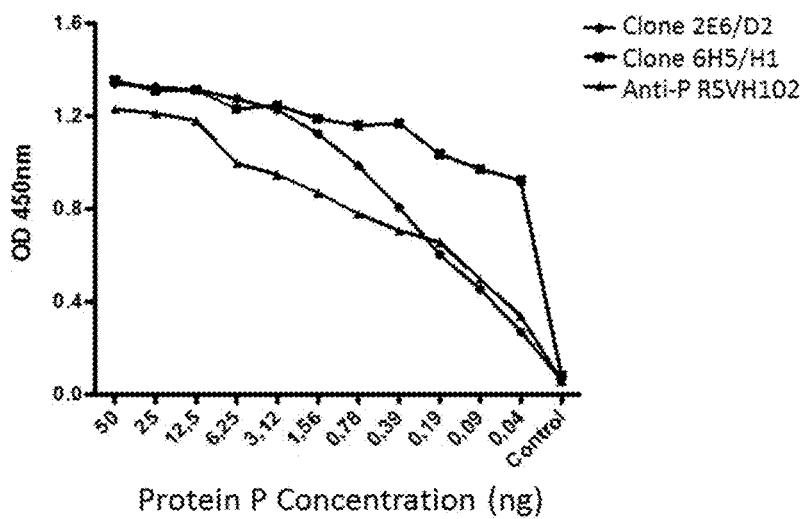
FIG. 2: Determination of sensitivity of monoclonal antibodies produced by the hybridomas 2E6/D2 and 6H5/H1 in the detection of the protein P of RSV. ELISA plates were activated with serial dilutions 1:2, starting with 50 ng of protein P and finalizing with 0.04 ng (A) and serial dilutions 1:2 starting with an inoculum $1 \times 10^5$ pfu of RSV to the dilution 1:5. 120 (B). Unactivated wells were included as negative control. The data shown in the plot chart express the absorbance to 450 nm emitted by the Horseradish peroxidase (HRP) enzyme present in the anti-P antibodies from the hybridomas 2E6/D2 and 6H5/H1, which were used in amount of 170 ng/well (A and B). The anti-P RSVH102 of RSV, catalogue number #AB94965, of Abcam, was also used in a concentration of 170 ng/well (A and B). The values correspond to the average of the emitted absorbance for each sample, in at least two independent assays.
Figure 2:
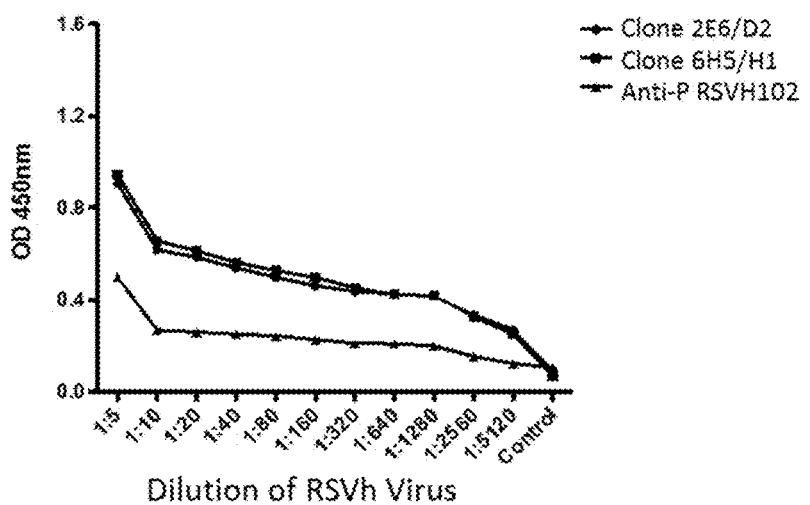

Example 5: Assay for Determining the Sensitivity of the Monoclonal Antibodies for Detection of Viral Antigens The assay was made for determining the maximum dilution of protein and virus of the RSV anti-P monoclonal antibodies from the hybridomas 2E6/D2 and 6H5/H1 are able of detecting using indirect ELISA. For this, was used the same technique described in the example 4. The plate was activated with 11 serial dilutions 1:2 of RSV protein P, starting with 50 ng of purified antigen. Respecting to the virus, the plate was activated with serial dilutions of 1:2, starting from $1 \times 10^5$ pfu of virus. The anti-P 2E6/D2 or 6H5/H1 antibodies, were used in a concentration of 3.4 µg/ml (170 ng/well), diluted in PBS/FBS 10%. Later the mouse anti-IgG detection antibody in a dilution of 1:2,000 (25 ng/well). The results showed that the antibody anti-P 2E6/D2 is able of recognizing until 40 picograms (pg) of the RSV protein P. The anti-P antibody from the hybridoma 6H5/H1, was more sensitive and detected until the last dilution of RSV protein P with greater intensity in the captured signal (FIG. 2A). The anti-P RSVH102 antibody, #AB94965 of Abcam, was also able of recognizing all the dilutions of the RSV protein P but with lower efficiency than the anti-P antibody from the hybridoma 6H5/H1.

Regarding the sensitivity of the antibodies represented in their capacity of detecting the RSV in high dilutions, it can be observed that the anti-P antibodies from the hybridoma 2E6/D2 can detect all the dilutions made of the virus, the same way the antibody from the hybridoma 6H5/H1, which would be equivalent to a 390 viral particles approximately. The two monoclonal antibodies are more efficient than the commercial RSV anti-P antibody, which detects until a dilution 1:40 (FIG. 2B).

In all the control assays were included which allow discard unspecific reactions of the antibodies, which contained all the assay components, excepting the sample (RSV protein P or virus).

Figure 3:
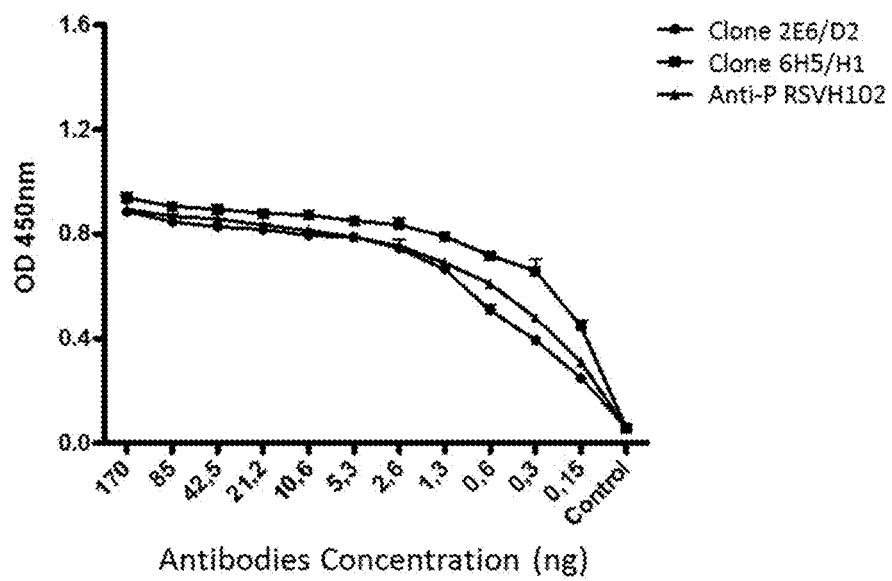
FIG. 3: Serial dilutions assay of the RSV anti-P monoclonal antibodies produced by the hybridomas 2E6/D2 and 6H5/H1, for the RSV purified antigens detection. ELISA plates were activated with 50 ng of RSV recombinant protein P and the antigen was detected with serial dilutions 1:2 of the anti-P antibodies 2E6/D1 or 6H5/H1, starting from a concentration of 3.4 µg/ml (170 ng/well). The data is expressed as the average of the emitted absorbance value to 450 nm of each sample in duplicate, in at least two independents assays.

Example 6: Assay for Detecting the Efficiency of the Monoclonal Antibodies for Detecting Viral Antigens The assay was made for determining the maximum dilution of the monoclonal antibodies RSV anti-P from the hybridomas 2E6/D2 and 6H5/H1, which allow the detection of the viral antigen using ELISA. For this, the same indirect ELISA technique was used of the example 6. The well was activated with 50 ng of the purified antigen and the anti-P antibodies 2E6/D2 or 6H5/H1 were used in dilutions 1:2, starting from the concentration of work (3.4 µg/ml) to the dilution 11 in PBS/FBS 10%. In FIG. 3 is observed that to all the dilutions, which were used in the assay, the anti-P 2E6/D2 and 6H5/H1 antibodies are able of detecting the RSV protein P. The anti-P RSVH102 antibody, catalogue number #AB94965, of Abcam, was also able of detecting in all the dilutions the RSV protein P, but it was less efficient than the anti-P 6H5/H1 antibody.

The negative control included on this assay, correspond to a well which does not contain sample (protein P), it was blocked with PBS/FBS 10%, primary antibody was not added (anti-P 2E6/D2 or anti-P 6H5/H1) and it contains only the mouse anti-IgG antibody conjugated with HRP.

Figure 6:
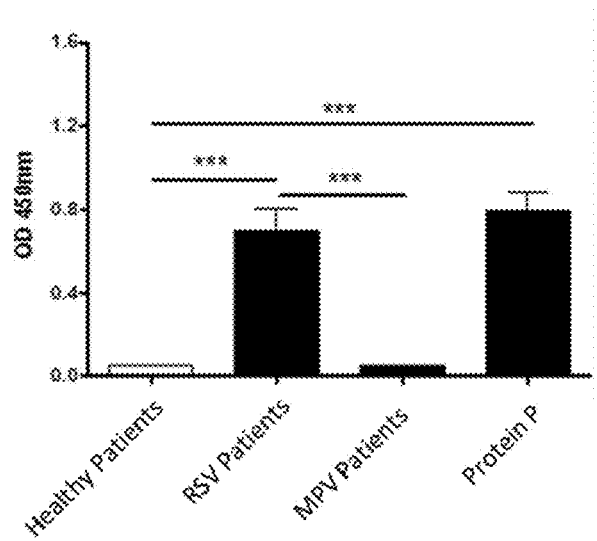
FIG. 6: RSV detection in clinical samples using ELISA in sandwich, using the combination of monoclonal antibodies secreted by the hybridomas 2E6/D, 6H5/H1 and the antibody RSVH102, catalogue number #AB94965, of Abcam. ELISA plates were activated with 170 ng of antibody secreted by the hybridoma 2E6/D2 (A) or the antibody anti-P RSVH102, catalogue number #AB94965, of Abcam (B), working as capture antibody. The wells activated with the capture antibody were incubated with 50 µl of nasopharyngeal swab (HNF) samples of patients which presented viral respiratory symptoms. As negative controls 10 (A) and 3 (B) samples of healthy patients were analyzed. Were used 20 (A) and 5 (B) samples of positive patients for RSV and, as specificity control, 20 (A) and 5 (B) samples of positive patients for the Metapneumovirus. As positive control, wells were included to which purified RSV protein P was added. For detection of the captured protein by the 2E6/D2 antibody or the anti-P RSVH102 commercial antibody, were used the antibodies produced by the hybridoma 6H5/H1 (A and B) and 2E6/D2 (B), conjugated to the Horseradish Peroxidase enzyme, in a dilution 1:2.000 (75 ng per well). The shown data are the average+/− the standard deviation of the absorbance value emitted to 450 n, of each sample (*$P<0.05$;  $P<0.001$; *$P<0.0001$ and ns there is not significate difference; using the ANOVA test of one via compared to positive patients for MPV or healthy patients).
Figure 6:
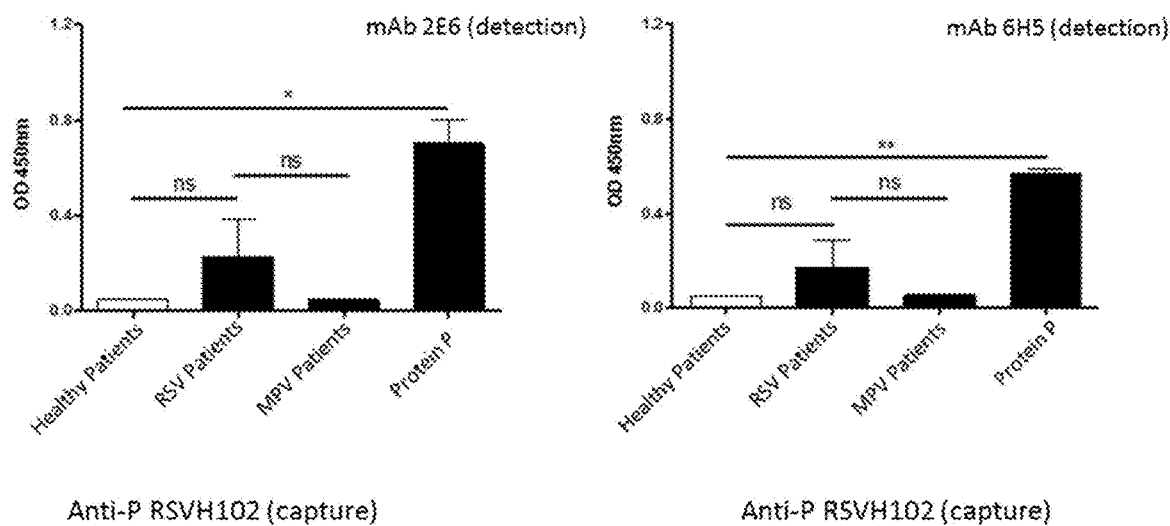

Example 7: Clinical Diagnostic of Patient Samples Infected with RSV, Using RSV Anti-P Monoclonal Antibody Using the ELISA Technique in Sandwich Due to the availability and concentration of the viral proteins in clinical samples obtained from nasopharyngeal swabs is low, it was needed modify the detection method and using the ELISA method in sandwich, using as capture antibody the anti-P antibody from the hybridoma 2E6/D2 or the RSV anti-P antibody RSVH102, catalogue number #AB94965, of Abcam. As antibody of detection the antibodies secreted by the clone anti-P 6H5/H1 or the clone anti-P 2E6/D2 were used, conjugated with HRP. For the assay, wells of an ELISA plate were activated with 3.4 µg/ml (170 ng/well) the anti-P antibody from the hybridoma 2E6/D2 or the RSV anti-P antibody RSVH102, catalogue number #AB94965, of Abcam, diluted in PBS, during 1 hour to 37° C. 2 washes were made with PBS-TWEEN 20® to the 0.05% and later the plate was blocked with 200 µL of PBS/FBS to the 10% during 2 hours to 37° C. It was washed again and it was incubated all night long to 4° C. each well with 50 µL of nasopharyngeal aspirates of positive patients for RSV according to the diagnostic method "D³ Ultra DFA Respiratory Virus Screening and ID Kit de DHI (Diagnostics Hibryds) USA", denominated in a routine way as "viral panel", and which were treated as they are described below*. As controls were included: 1) specificity control (50 µL of patient samples diagnosed with MPV using the viral panel), 2) positive control (50 ng of recombinant RSV protein P) and 3) negative control corresponding to healthy patient samples (negatives for virus using the viral panel). To the following day, the washes were made and each well was incubated by 1 hour to 25° C. with 50 µL of the anti-P antibody from the hybridoma 6H5/H1 or 2E6/D2 conjugated with HRP. The plate was washed twice and it was revealed with 50 µL of solution TMB, it was incubated from 10 to 15 minutes in the dark. The reaction was stopped with 504 of $H_2SO_4$ 2N. The reading of the plate was made in an ELISA lector Epoch, certified for clinical diagnostic. The obtained results for this assay are shown in the FIG. 6, where it can be observed that the ELISA technique in sandwich using the antibody from the hybridoma 2E6/D2 as capture antibody and the antibody from the hybridoma 6H5/H1-HRP as detection antibody, allows detecting the antigen in samples of patients infected with RSV (FIG. 6A), which were previously confirmed by direct immunofluorescence in a certified clinical laboratory, using the viral panel. The number of patients included in the assay was 20, of which 17 were detected as positive by ELISA with an optical density (OD) above 0.1. This assay demonstrates also the versatility that present the antibodies from the hybridomas 2E6/D2 and 6H5/H1, since they are able of binding simultaneously to the antigen without competing nor interfere with each, allowing the capture and later detection of the protein P in samples of patients. In the FIG. 6B are shown the obtained results with the commercial capture antibody and the two anti-P clones 6H5/H1 and 2E6/D2 of detection antibodies. The results show that of a total of 5 positive patients for RSV, just 1 was detected in ELISA in Sandwich, for both the combination of the RSV anti-P antibody RSVH102, catalogue number #AB94965, of Abcam of capture with the anti-P 6H5/H1 clone and with the clone 2E6/D2. These results show the high efficiency of the monoclonal antibodies of the invention in the detection of the virus in clinical samples comparing the RSV anti-P antibody RSVH102, catalogue number #AB94965, of Abcam.

*: Clinical samples treatment. The samples used for the assays were obtained from the nasopharyngeal swabs contained in universal transport medium. The samples were spin-dried o 2,000 rpm during 10 minutes to 4° C. Lately, the supernatant was separated (SN1) from the pellet; the latter was incubated with 1004 of Buffer RIPA (50 mM Tris-HCl pH 8.0, 150 mM NaCl, 1% NP-40, 0,5% Sodium deoxycholate, 0,1%, SDS in a proteases inhibitors cocktail) during 15 minutes to 4° C., shaking by vortex every 5 minutes. Following it was spin-dried to 2,000 rpm during 10 minutes to 4° C. At the end, the obtained supernatant was taken (SN2) and was mixed with the SN1.

Figure 4:
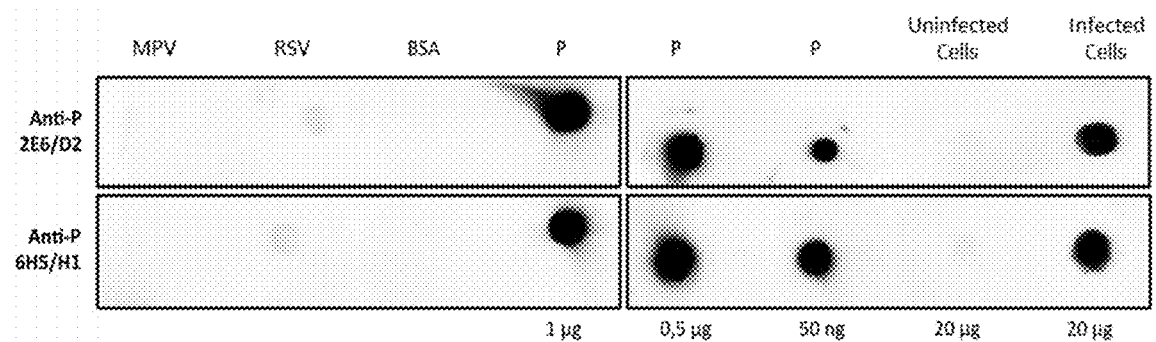
FIG. 4: Confirmation of specificity of monoclonal antibodies secreted by the hybridomas 2E6/D2 and 6H5/H1, using dot blot. The RSV anti-P antibodies produced by the hybridomas 2E6/D2 or 6H5/H1 were incubated by 1 hour with a nitrocellulose membrane which contained the following immobilized samples (in stains form or "dots"): MPV ($1\times10^6$ PFU), RSV ($1\times10^6$ PFU), BSA (1 µg), protein P of RSV (1 µg, 500 ng y 50 ng), y 20 µg of extract of cells HEp-2 without infecting, or infected with RSV. After the incubation, the membrane was washed and was incubated by 1 hour with a mouse anti-IgG secondary antibody conjugated with the protein HRP. After the incubation, the visualization of the binding of the monoclonal antibodies to the antigen was performed using the capture of the chemiluminescence produced by the catalysis of the commercial substrate "enhanced chemiluminescence Western blot detection system" (ECL, Amersham, Uppsala, Sweden). It is observed that the antibodies produced by the hybridoma 2E6/D2 or 6H5/H1 are binding just to the dots where is present the protein P of RSV, the RSV virus and infected cells with RSV, confirming the specificity of these antibodies.

Example 8: Assay of Specificity of the RSV Anti-P Monoclonal Antibodies for RSV Purified Antigens, Using the Dot-Blot Assay This assay has as objective confirming the specificity by the RSV protein P of the antibodies produced by the hybridomas 2E6/D2 and 6H5/H1, using the methodology of immunoblot. The antigen detection was carried out using the dot-blot technique, where a nitrocellulose membrane is used as solid support for immobilizing the antigen present in a suspension drop. For this, it was deposited over the membrane of nitrocellulose 20 µl containing each one: $1\times10^6$ pfu of MPV, $1\times10^6$ pfu of RSV, purified RSV protein P (1 µg, 500 ng and 50 ng), 20 µg of cells extract HEp-2 infected with RSV and 20 µg of cells extract HEp-2 uninfected. As negative control 500 ng of BSA were applied, contained in 20 µl. It was allowed that the applied solutions over the membrane were air dried by 15 minutes. Lately, the membrane was blocked with BSA to the 5% in PBS containing TWEEN-20® 0.05%, for 1 h to 25° C. The membranes were incubated with 3.4 µg/ml of anti-P monoclonal antibody from the hybridoma 2E6/D2 or of the hybridoma 6H5/H1 in block solution for 1 h to 25° C. Then the non-adhered to the antigen antibody excess was removed using three washes with PBS-Tween-20 0.05% to 25° C. The detection of the antibodies bound to the antigen was made using a mouse anti-IgG antibody conjugated to HRP (Invitrogen, Life Technologies #62-6520). This was incubated for 1 h in blocking solution to 25° C., for lately removing the excess of non-bound antibody using three washes with PBS-Tween-20 0.05% to 25° C. The visualization of the binding of the monoclonal antibodies to the antigen was made using the capture of the chemiluminescence produced for the catalysis of commercial substrate "enhanced chemiluminescence Western blot detection system" (ECL, Amersham, Uppsala, Sweden), mediated for the enzyme HRP bound to the mouse anti-IgG antibody. The capture of the chemiluminescence was made in the photodocumentation MyECL (Thermo Fisher). It is observed in the FIG. 4, the antibodies from the hybridomas 2E6/D2 and 6H5/H1 are just bound to the "dots" containing RSV or protein P, and they do not binding of unspecific way to the "dots" containing the non-related proteins, other viruses or uninfected cells.

Figure 5:
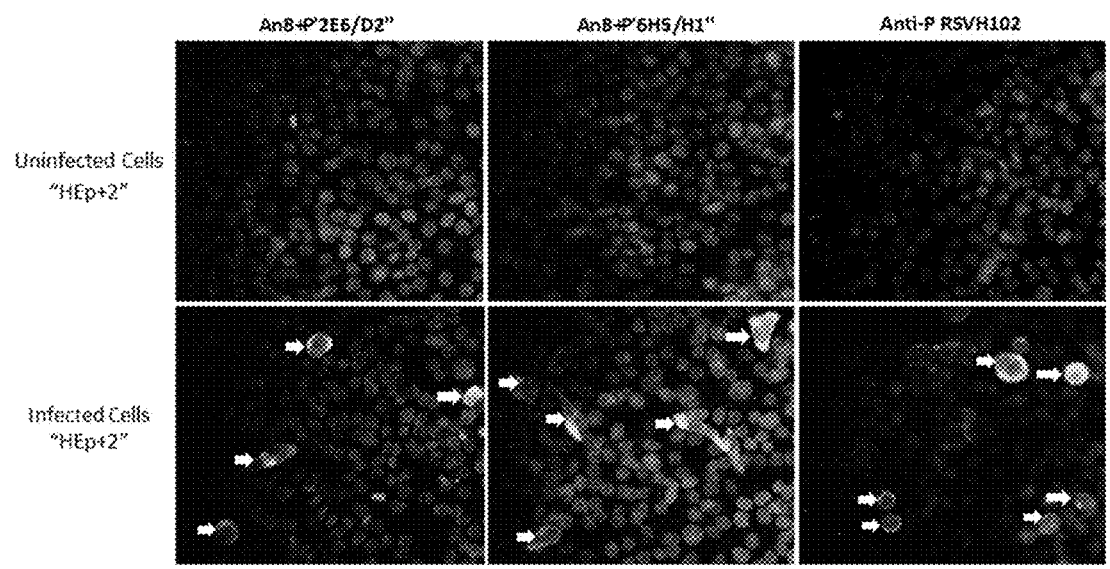
FIG. 5: Detection of the protein P-RSV by immunofluorescence in cells HEp-2 infected with RSV. Cells HEp-2 were grown in vitro until approach confluence (between 70-90%), to be infected by 48 hours with RSV. Lately, they were fixed with paraformaldehyde and prepared for indirect immunofluorescence. For this was used as primary monoclonal antibody derived from hybridoma 2E6/D2, of the hybridoma 6H5/H1 of the RSVH102 anti-P antibody, catalogue number #AB94965, of Abcam. As secondary antibody was used a mouse anti-IgG commercial antibody conjugated to the fluorophore Alexa Fluor 488, which emits fluorescence to 519 nm (intense sign). The cell core was dyed with the fluorophore TOPRO-3 iodide, which emits fluorescence to 661 nm (light gray circles observed in not infected cells and infected cells). A strong reactivity is observed in the cytoplasm (intense white sign, indicated with white arrows) only in infected cells when any of the three primary antibodies is used.

Example 9: Detection of Infection for RSV in Cells HEp-2 by Immunofluorescence, Using RSV Anti-P Monoclonal Antibodies This assay was made for amplifying the techniques spectrum, which allows detecting the infection for RSV, using the described invention. An assay was carried out for fluorescence microscopy, where infected or uninfected with RSV cells HEp-2 were incubated with the RSV anti-P monoclonal antibodies derivated from the hybridomas 2E6/D2 or 6H5/H1. The used protocol was the following: the cells fixed with paraformaldehyde 4% diluted in PBS, for 10 minutes to 25° C. Then, the cells were washed with PBS and were permeabilized with saponin 0.2% diluted in PBS/FBS 10% for 30 minutes to 25° C. The monoclonal antibodies derivated from the hybridomas 2E6/D2 or 6H5/H1 were added to a concentration of 3.4 µg/ml, diluted in PBS/FBS 10% for 1 hour to 25° C. Lately, two washes with PBS were made and the mouse anti-IgG secondary antibody was added, conjugated to the fluorophore Alexa fluor 488 (Life Technologies), in dilution 1 in 200 in PBS/FBS 10% for 1 hour to 25° C., in darkness. The washes were repeated and the cores with TOPRO-3 iodide 642/661 (Invitrogen, #T3605) were dyed to a dilution 1:5,000 for 15 minutes to 25° C., in darkness. Lastly, it was washed with PBS and the coverslip was mounted for later observation in an epifluorescence microscope. The obtained results show that the constituent antibodies of the invention are also useful for recognizing specifically infected cells using immunofluorescence, without binding in unspecific way to uninfected cells (FIG. 5).

The described examples in this specification demonstrate the specificity, efficiency, Zo sensitivity and versatility that have these RSV anti-P monoclonal antibodies secreted by the cells lines of the hybridomas 2E6/D2 and 6H5/H1. The examples presented herein constituent a demonstration of some of the uses of the RSV anti-P monoclonal antibodies, but in no case they limit the scope of the present invention.

---

The invention claimed is:

1. A monoclonal antibody or a functional fragment thereof that binds to a protein P of a human Respiratory Syncytial Virus (RSV), wherein the monoclonal antibody or the functional fragment thereof comprises a heavy chain variable region and a light chain variable region, wherein the heavy chain variable region is SEQ ID No: 5 and the light chain variable region is SEQ ID No: 6.

2. The monoclonal antibody or the functional fragment thereof according to claim 1, wherein the antibody or the functional fragment thereof is also bound to a label which allows for the antibody's or the functional fragment's detection, selected from the group consisting of fluorophores, biotin, radioisotopes, metals and enzymes.

3. A set of nucleotide sequences which encode the monoclonal antibody or the functional fragment thereof according to claim 1, wherein the monoclonal antibody or the functional fragment thereof comprises a heavy chain variable region and a light chain variable region, wherein the heavy chain variable region is SEQ ID No:5 and the light chain variable region is SEQ ID No:6, wherein the nucleotide sequences that encode the monoclonal antibody or the functional fragment thereof comprises a nucleotide sequence of SEQ ID No:7 and a reverse complement encoding the heavy chain variable region of the antibody, and a nucleotide sequence of SEQ ID No:8 and a reverse complement, encoding the light chain variable region of the antibody.

4. An in vitro and/or ex vivo method for diagnosing a respiratory infection by RSV in a biological sample, wherein the method comprises:
contacting the biological sample with the monoclonal antibody against the RSV protein P or the functional fragment thereof according to claim 1 wherein the monoclonal antibody or the functional fragment thereof comprises a heavy chain variable region and a light chain variable region, wherein the heavy chain variable region is SEQ ID No:5 and the light chain variable region is SEQ ID No:6; and
detecting antibody-antigen binding.

5. The in vitro and/or ex vivo method for diagnosing according to claim 4, wherein the biological sample is selected from the group consisting of in vitro cells infected with RSV, nasal secretions, nasal washes, pharyngeal secretions and bronchial washes or secretions.

6. The in vitro and/or ex vivo method for diagnosing according to claim 4, wherein the assay used for the detection of the binding of the antibody to the antigen is selected from the group consisting of ELISA, immunofluorescence, immunohistochemistry, immunochromatography, flow cytometry, cell sorter, immunoprecipitation and Western blot.

7. The in vitro and/or ex vivo method for diagnosing according to claim 4, wherein the antibody or functional fragment thereof is conjugated with a label that allows for the antibody's or the functional fragment's detection.

8. The in vitro and/or ex vivo method for diagnosing according to claim 7, wherein the label is selected from the group consisting of fluorophores, biotin, radioisotopes, metals and enzymes.

9. The in vitro and/or ex vivo method for diagnosing according to claim 7, wherein the antibody is attached to a solid support.

10. The in vitro and/or ex vivo method for diagnosing according to claim 7, wherein the solid support is a membrane formed by one of the compounds selected from the group consisting of nitrocellulose, cellulose, polyethylene and nylon.

11. A diagnostic kit for detecting RSV, wherein the kit comprises the monoclonal antibody against RSV according to claim 1, wherein the monoclonal antibody or the functional fragment thereof comprises a heavy chain variable region and a light chain variable region, wherein the heavy chain variable region is SEQ ID No:5 and the light chain variable region is SEQ ID No:6.

12. The diagnostic kit according to claim 11, wherein the antibody is attached to a solid support.

13. The diagnostic kit according to claim 12, wherein the solid support is a membrane formed by one of the compounds selected from the group consisting of nitrocellulose, cellulose, polyethylene and nylon.

14. The diagnostic kit according to claim 11, wherein the diagnostic kit further comprises an immunochromatographic test, multiple immunoassays, flow cytometry, immunofluorescence, radioimmunoassay, Western blot, Dot plot, ELISA, immunodifusion or immunoprecipitation, for detecting RSV.

* * * * *

SEQUENCE LISTING

```
<160> NUMBER OF SEQ ID NOS: 12

<210> SEQ ID NO 1
<211> LENGTH: 153
<212> TYPE: PRT
<213> ORGANISM: Artificial Sequence
<220> FEATURE:
<223> OTHER INFORMATION: Synthetic - Hibridoma 2E6/D2 - anti-P VH

<400> SEQUENCE: 1

Met Glu Trp Ser Trp Val Phe Leu Phe Leu Met Ala Gln Ser Gly Pro
1               5                   10                  15

Glu Leu Val Arg Pro Gly Ala Ser Val Lys Met Ser Cys Lys Ala Ser
                20                  25                  30

Gly Tyr Thr Phe Thr Ser Ser Trp Met His Trp Val Lys Gln Arg Pro
            35                  40                  45

Gly Gln Gly Leu Glu Trp Met Arg Gln Arg Pro Glu Gln Gly Leu Glu
        50                  55                  60

Trp Leu Gly Arg Ile Asp Pro Ala Asn Gly Asn Ser Lys Tyr Asp Pro
65                  70                  75                  80

Lys Phe Gln Gly Lys Ala Thr Ile Thr Ala Asp Thr Ser Ser Asn Thr
                85                  90                  95

Ala Tyr Leu Gln Leu Ser Ser Leu Gly Ser Tyr Thr Tyr Tyr Pro Asp
            100                 105                 110

Ser Val Lys Gly Arg Phe Thr Ile Ser Arg Asp Asn Ala Lys Asn Ser
        115                 120                 125

Leu Tyr Leu Gln Met Ser Ser Leu Arg Ser Pro Ser Val Tyr Pro Leu
    130                 135                 140

Ala Pro Gly Ser Leu Gly Ile Thr Ser
145                 150

<210> SEQ ID NO 2
<211> LENGTH: 152
<212> TYPE: PRT
<213> ORGANISM: Artificial Sequence
<220> FEATURE:
<223> OTHER INFORMATION: Synthetic - Hibridoma 2E6/D2 - anti-P VL

<400> SEQUENCE: 2

Met Glu Ser Asp Thr Asp Thr Leu Leu Leu Trp Val Leu Leu Leu Trp
1               5                   10                  15

Val Pro Gly Ser Thr Gly Asp Ile Val Leu Thr Gln Ser Pro Ala Ser
                20                  25                  30

Leu Ala Val Ser Leu Gly Gln Arg Ala Thr Ile Ser Tyr Arg Ala Ser
            35                  40                  45

Val Ser Thr Ser Gly Tyr Ser Tyr Met His Trp Asn Gln Gln Lys Pro
```

```
                50                  55                  60
Gly Gln Pro Pro Arg Leu Leu Ile Tyr Leu Val Ser Asn Leu Glu Ser
 65                  70                  75                  80

Gly Val Pro Ala Arg Phe Ser Gly Ser Gly Ser Gly Thr Asp Phe Thr
                 85                  90                  95

Leu Asn Ile His Pro Val Glu Glu Gln Leu Ser Ser Leu Thr Ser Tyr
            100                 105                 110

Gln Gln Thr His Pro Thr Gln Pro Thr Cys Asn Ser Ala Ala Trp
        115                 120                 125

His Leu Arg Thr Leu Pro Ser Ile Thr Val Arg Ala Ala Ser Thr Cys
        130                 135                 140

Gly His Pro Val Ser Leu Gly Ile
145                 150

<210> SEQ ID NO 3
<211> LENGTH: 459
<212> TYPE: DNA
<213> ORGANISM: Artificial Sequence
<220> FEATURE:
<223> OTHER INFORMATION: Synthetic - Hibridoma 2E6/D2 - anti-P VH

<400> SEQUENCE: 3
atggaatgga gctgggtctt cctcttcctg atggcacagt ctgggcctga gctggtgagg      60
cctggggctt cagtgaagat gtcctgcaag gcttcaggct ataccttcac cagctcctgg     120
atgcactggg tgaaacagag gcctggacaa ggccttgagt ggatgaggca gaggcctgaa     180
cagggcctgg agtggcttgg aggattgat cctgcgaatg gtaattctaa atatgacccg      240
aagttccagg gcaaggccac tataacagca gacacatcct ccaacacagc ctacctgcaa     300
ctcagcagcc tggtagtta tacctactat ccagacagtg tgaaggggcg attcaccatc      360
tccagagaca atgccaagaa ttccctatac ctgcaaatga gcagtctgag gtctccatcc     420
gtctatcccc tggcccctgg aagcttggga atcactagt                            459

<210> SEQ ID NO 4
<211> LENGTH: 456
<212> TYPE: DNA
<213> ORGANISM: Artificial Sequence
<220> FEATURE:
<223> OTHER INFORMATION: Synthetic - Hibridoma 2E6/D2 - anti-P VL

<400> SEQUENCE: 4
atggagtcag acacagacac actcctgcta tgggtactgc tgctctgggt tccaggttcc      60
actggtgaca ttgtgctgac acagtctcct gcttccttag ctgtatctct ggggcagagg     120
gccaccatct catacagggc cagtgtcagt acatctggct atagttatat gcactggaac     180
caacagaaac caggacagcc acccagactc ctcatctatc ttgtatccaa cctagaatct     240
ggggtccctg ccaggttcag tggcagtggg tctgggacag acttcaccct caacatccat     300
cctgtggagg agcaactcag cagcctgaca tcttaccaga gacacatcc tccaacacag      360 cctacctgca actcagcagc ctggcatctg aggacactgc cgtctattac tgtgcgagcg     420
gcttctactt gcggacatcc agtaagcttg ggaatc                               456

<210> SEQ ID NO 5
<211> LENGTH: 154
<212> TYPE: PRT
<213> ORGANISM: Artificial Sequence
<220> FEATURE:
<223> OTHER INFORMATION: Synthetic - Hibridoma 6H5/H1 - anti-P VH
```

<400> SEQUENCE: 5

Met Glu Trp Ser Arg Gln Arg Pro Glu Gln Gly Leu Glu Trp Leu Gly
1               5                   10                  15

Arg Ile Asp Pro Ala Asn Gly Asn Ser Lys Tyr Asp Pro Lys Phe Gln
            20                  25                  30

Gly Lys Ala Thr Ile Thr Ala Asp Thr Ser Ser Asn Thr Ala Tyr Ser
        35                  40                  45

Cys Thr Ala Ser Gly Phe Asn Ile Thr Gln Ser Pro Ala Ser Leu Ala
    50                  55                  60

Val Ser Leu Gly Gln Arg Ala Thr Ile Ser Tyr Arg Ala Ser Lys Ser
65                  70                  75                  80

Val Ser Thr Ser Gly Tyr Ser Tyr Met His Trp Asn Gln Gln Lys Pro
                85                  90                  95

Gly Met Ala Ser Gly Phe Thr Phe Ser His Tyr Ala Met Ser Trp Ala
            100                 105                 110

Arg Gln Thr Pro Glu Lys Gln Gln Ser Gly Pro Glu Leu Val Arg Pro
        115                 120                 125

Gly Ala Ser Val Val Thr Val Ser Ala Ala Lys Thr Thr Pro Pro Pro
    130                 135                 140

Val Tyr Ala Leu Gly Pro Trp Lys Leu Gly
145                 150

<210> SEQ ID NO 6
<211> LENGTH: 121
<212> TYPE: PRT
<213> ORGANISM: Artificial Sequence
<220> FEATURE:
<223> OTHER INFORMATION: Synthetic - Hibridoma 6H5/H1 - anti-P VL

<400> SEQUENCE: 6

Met Glu Ser Asp Thr Leu Leu Thr Gly Asp Ile Val Leu Thr Gln Ser
1               5                   10                  15

Pro Ala Ser Leu Ala Val Ser Leu Gly Gln Arg Ala Thr Gly Asp Ile
            20                  25                  30

Val Leu Thr Gln Ser Pro Ala Ser Leu Ala Val Ser Leu Gly Gln Arg
        35                  40                  45

Ala Thr Ile Ser Tyr Arg Ala Ser Lys Ser Val Ser Thr Ser Gly Tyr
    50                  55                  60

Ser Tyr Met His Trp Asn Gln Gln Lys Pro Gly Gln Pro Pro Arg Leu
65                  70                  75                  80

Leu Ile Tyr Leu Val Ser Asn Leu Glu Ser Gly Val Pro Ile Arg Glu
                85                  90                  95

Leu Thr Arg Ser Glu Gly Gly Pro Ser Trp Lys Tyr Ser Ser Ser Ile
            100                 105                 110

Phe Pro Pro Ser Ser Lys Leu Gly Asn
        115                 120

<210> SEQ ID NO 7
<211> LENGTH: 462
<212> TYPE: DNA
<213> ORGANISM: Artificial Sequence
<220> FEATURE:
<223> OTHER INFORMATION: Synthetic - Hibridoma 6H5/H1 - anti-P VH

<400> SEQUENCE: 7
atggaatgga gcaggcagag gcctgaacag ggcctggagt ggcttgggag gattgatcct      60

```
gcgaatggta attctaaata tgacccgaag ttccagggca aggccactat aacagcagac      120
acatcctcca acacagccta ctcctgcaca gcttctggct tcaacattac acagtctcct      180
gcttccttag ctgtatctct ggggcagagg gccaccatct catacagggc cagcaaaagt      240
gtcagtacat ctggctatag ttatatgcac tggaaccaac agaaaccagg aatggcctct      300
ggattcactt tcagtcacta tgccatgtct tgggctcgcc agactccgga gaagcagcag      360
tctgggcctg agctggtgag gcctgggggct cagtggtca ctgtctctgc agccaaaaca      420 acaccccac ccgtctatgc ccttggcccc tggaagcttg gg                          462

<210> SEQ ID NO 8
<211> LENGTH: 363
<212> TYPE: DNA
<213> ORGANISM: Artificial Sequence
<220> FEATURE:
<223> OTHER INFORMATION: Synthetic - Hibridoma 6H5/H1 - anti-P VL

<400> SEQUENCE: 8
atggagtcag acacactgct gactggtgac attgtgctga cacagtctcc tgcttcctta      60
gctgtatctc tggggcagag ggccactggt gacattgtgc tgacacagtc tcctgcttcc      120
ttagctgtat ctctggggca gagggccacc atctcataca gggccagcaa aagtgtcagt      180
acatctggct atagttatat gcactggaac caacagaaac caggacagcc acccagactc      240
ctcatctatc ttgtatccaa cctagaatct ggggtcccta ttaggagct acacgttcg       300 gagggggggac caagctggaa atattcatct tccatcttcc caccatccag taagcttggg      360
aat                                                                   363

<210> SEQ ID NO 9
<211> LENGTH: 33
<212> TYPE: DNA
<213> ORGANISM: Artificial Sequence
<220> FEATURE:
<223> OTHER INFORMATION: Synthetic - Nucleotides of primer MuIgkVL5'-B

<400> SEQUENCE: 9
gggaattcat ggagacagac acactcctgc tat                                   33

<210> SEQ ID NO 10
<211> LENGTH: 39
<212> TYPE: DNA
<213> ORGANISM: Artificial Sequence
<220> FEATURE:
<223> OTHER INFORMATION: Synthetic - Nucleotides of primer MuIgkVL5'-C

<400> SEQUENCE: 10
actagtcgac atggagwcag acacactsct gytatgggt                             39

<210> SEQ ID NO 11
<211> LENGTH: 33
<212> TYPE: DNA
<213> ORGANISM: Artificial Sequence
<220> FEATURE:
<223> OTHER INFORMATION: Synthetic - Nucleotides of primer MuIgVH5'-A

<400> SEQUENCE: 11
gggaattcat grasttskgg ytmarctkgr ttt                                   33

<210> SEQ ID NO 12
<211> LENGTH: 35
<212> TYPE: DNA
<213> ORGANISM: Artificial Sequence
```

```
<220> FEATURE:
<223> OTHER INFORMATION: Synthetic - Nucleotides of primer MuIgVH5'-F

<400> SEQUENCE: 12
actagtcgac atgaacttyg ggytsagmtt grttt                              35
```